(12) United States Patent
Heinze et al.

(10) Patent No.: US 10,233,260 B2
(45) Date of Patent: Mar. 19, 2019

(54) PROCESS FOR THE FUNCTIONALIZATION OF A SURFACE

(71) Applicant: fzmb GmbH Forschungszentrum fuer Medizintechnik und Biotechnologie, Bad Langensalza (DE)

(72) Inventors: Thomas Heinze, Jena (DE); Holger Wondraczek, Turku (FI); Thomas Elschner, Jena (DE); Friedrich Scholz, Jena (DE)

(73) Assignee: FZMB GMBH Forschungszentrum Fuer Medizintechnik Und Biotechnologie, Bad Langensalza (DE)

( * ) Notice: Subject to any disclaimer, the term of this patent is extended or adjusted under 35 U.S.C. 154(b) by 437 days.

(21) Appl. No.: 14/772,443

(22) PCT Filed: Mar. 20, 2014

(86) PCT No.: PCT/EP2014/055584
§ 371 (c)(1),
(2) Date: Sep. 3, 2015

(87) PCT Pub. No.: WO2014/147168
PCT Pub. Date: Sep. 25, 2014

(65) Prior Publication Data
US 2016/0009825 A1    Jan. 14, 2016

(30) Foreign Application Priority Data
Mar. 20, 2013  (DE) .................. 10 2013 005 184

(51) Int. Cl.
| | |
|---|---|
| C08B 15/06 | (2006.01) |
| C07H 13/12 | (2006.01) |
| C09D 101/08 | (2006.01) |
| C08J 7/04 | (2006.01) |
| C03C 17/32 | (2006.01) |
| C08J 7/12 | (2006.01) |

(52) U.S. Cl.
CPC .............. C08B 15/06 (2013.01); C03C 17/32 (2013.01); C07H 13/12 (2013.01); C08J 7/047 (2013.01); C08J 7/12 (2013.01); C09D 101/08 (2013.01); *C08J 2323/04* (2013.01); *C08J 2323/06* (2013.01); *C08J 2401/08* (2013.01)

(58) Field of Classification Search
CPC .... C08B 15/06; C08J 7/047; C08J 7/12; C08J 2401/08; C07H 13/12; C09D 101/02; C09D 101/08; C09D 103/04; C09D 103/14; C09D 105/08
See application file for complete search history.

(56) References Cited

U.S. PATENT DOCUMENTS

| | | |
|---|---|---|
| 5,728,751 A | 3/1998 | Patnaik |
| 2009/0216006 A1* | 8/2009 | Xu .......................... C08B 15/06 536/55.3 |
| 2011/0251265 A1 | 10/2011 | Uludag et al. |

FOREIGN PATENT DOCUMENTS

| | | |
|---|---|---|
| DE | 3836599 | 5/1990 |
| DE | 102005008434 | 9/2006 |
| EP | 1222926 | 1/2002 |
| WO | 2006/089499 | 8/2006 |

OTHER PUBLICATIONS

Peter Forbes, Spektrum der Wissenschaft, Aug. 2009, pp. 88-95.
G. Menges et al., Menges Werkstoffkunde Kunststoffe, Carl Hanser Verlag, Munich 2011; p. 23.
K. Petzold-Weicke et al.: Unconventional Cellulose Products Through Nucleophilic Displacement Reactions, Macromolecular Symposia 280, 2009, 72-85.
P. Berlin et al.: A novel soluble aminocellulose derivative type: Its transparent film-forming properties and its efficient coupling with enzyme proteins for biosensors, Macromol. Chem. Phys. 2000, 201, 2070-2082.
P. Berlin et al.: Film-forming aminocellulose derivatives as enzyme-compatible support matrices for biosensor developments, Cellulose 2003, 10, 343-367.
S. Barker, H.M. Disney, P. Somers: The reaction of dextran carbonate with amino acids and polypeptides, Carbohydrate Research 1972, 25, 237-241.
M.S. Chaves, F. Arranz: Water-insoluble dextrans by grafting 2: Reaction of dextrans with normal-alkyl chloroformates, Chemical and enzymatic hydrolysis, Macromolecular Chemistry and Physics, 1985, 186, 17-29.
Sabrine Alila, Ana Maria Ferraria, Ana Maria Botelho do Rego, Sami Boufi: Controlled surface modification of cellulose fibers by amino derivatives using N,N-carbonyldiimidazole as activator, Carbohydrate Polymers 77, 2009, 553-562.
* cited by examiner

*Primary Examiner* — Roberto Rabago
(74) *Attorney, Agent, or Firm* — Jacobson Holman PLLC

(57) ABSTRACT

A functionalization is performed with a dissolved oligo- or polysaccharide derivative which contains at least one free functional group, especially an amino group, linked through a polar carbamate linkage and a spacer (X), according to the general formula I:

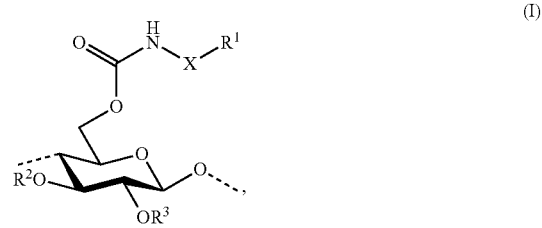

(I)

14 Claims, No Drawings

PROCESS FOR THE FUNCTIONALIZATION OF A SURFACE

The invention relates to a process for the functionalization of a surface, for example, of a substrate intended to have particular surface properties for chemical and biochemical applications, especially as a sample support for analytical purposes, or for immediate physical, chemical, biological and technical applications, for which the surface is to be provided with defined properties and functions. In particular, synthetic polymers and natural polymers, such as polysaccharides and proteins, paper, glass, ceramic, silicon, metals and metal oxides including magnetic materials are used as materials for such surfaces.

The modification of surfaces by physical and/or chemical processes is an important procedure for readily changing the properties of materials and adapt them to desired applications.

Plasma methods, for example, play an important role, but with the disadvantage that the surface alteration is not permanent.

Also, numerous methods are known in which inorganic or organic molecules are deposited and fixed on surfaces. Thus, for example, superhydrophilic or superhydrophobic surfaces can be prepared by depositing titanium oxide or silicon oxide (Peter Forbes, Spektrum der Wissenschaft, August 2009, pp. 88-95). Such surfaces are chemically inert. Different polymers are also employed for surface modification. The probably best known use relates to the polymeric varnish formers, which have long been used extensively. These also form non-reactive surfaces (G. Menges et al., Menges Werkstoffkunde Kunststoffe, Carl Hanser Verlag, Munich 2011, p. 23).

DE 10 2005 008 434 A1 describes so-called aminocelluloses, which can deposit on different materials, the amino groups being chemically reactive and suitable, for example, for the covalent fixation of enzymes. Such surfaces are supposed to enable the biocompatible finishing of materials and the development of bioassays, for example, through the binding of enzymes. The aminocelluloses described in WO 2006/089499 A1 are obtained by the well known reaction of cellulose p-toluenesulfonic acid esters with diamines or oligoamines according to a nucleophilic substitution reaction ($S_N$ reaction), in which the diamines or oligoamines must be employed at an enormous excess of 10 to 20 moles per mole of tosyl groups in order to obtain soluble products. Because of the mechanism of the $S_N 2$ reaction, 6-deoxy-6-aminocellulose derivatives with a maximum number of one amino substituent per repeating unit are formed, corresponding to an average degree of substitution (DS) of 1 (K. Petzold-Welcke et al.: Unconventional Cellulose Products Through Nucleophilic Displacement Reactions, Macromolecular Symposia 280, 2009, 72-85). The structure of the deoxy-amino bond involves a tetrahedral carbon atom ($sp^3$ carbon), which is problematic for interactions with surfaces because of its steric demand. In addition, the secondary nitrogen atom in the C—N bond is reactive and can be protonated, and therefore can lead to unmanageable side reactions and secondary structures.

Although the degree of substitution of cellulose derivatives can amount up to 3, maximum values of 0.8 are achieved in practice in this reaction. Thus, despite the numerous couplings on surfaces, which are possible in principle, only a relatively low number of amino groups are present on the surfaces in practice. The application of the unavoidable high excess of diamine or oligoamine in the production is not only economically inefficient, but additionally requires a tedious and cost-intensive purification of aminocellulose. Residues of diamine or oligoamine in the samples can lead to different undesirable side reactions including dangerous biological effects during the application, since diamine and oligoamine are known to tend to be biologically active. The properties of the 6-deoxy-6-aminocellulose derivatives, such as solubility in water or in an organic solvent, can be achieved only by complicated subsequent chemical methods, such as esterification or etherification of the remaining hydroxy groups. It is an additional disadvantage that tosyl groups are cleaved off uncontrollably by the subsequent chemical methods, and thus non-unitary structures with an unclear distribution of substituents are formed (P. Berlin et al.: A novel soluble aminocellulose derivative type: its transparent film-forming properties and its efficient coupling with enzyme proteins for biosensors, Macromol. Chem. Phys. 2000, 201, 2070-2082). In addition, the ester groups are also cleaved off uncontrollably during the $S_N$ reaction with the amines (P. Berlin et al.: Film-forming aminocellulose derivatives as enzyme-compatible support matrices for biosensor developments, Cellulose 2003, 10, 343-367).

According to EP 1 222 926 A1, amino groups are introduced into polysaccharides, preferably a branched dextran, by reductive amination. Thus, the polysaccharide is at first oxidized to the corresponding dialdehyde polysaccharide derivatives with cleavage of the repeating unit. In principle, a relatively high number of amino groups could be realized in the polymer with an average degree of substitution of 2, which is not achieved, however, because only partial oxidation of the dialdehyde is possible, and in addition, only part of the existing aldehyde groups react with the diamine or oligoamine. Neither the polysaccharide derivatives containing amino groups thus available from the branched dextran, nor those available from the unbranched cellulose exhibit adhesive properties. They can be employed as polycations in gene therapy. Unlike amino groups, the cationic ammonium groups are no longer chemically active, and are therefore unsuitable for the above mentioned applications.

Another process for the modification of materials proceeds from polymers activated by isocyanate groups (U.S. Pat. No. 5,728,751 A). It is very well known that isocyanates are extremely toxic compounds, which both precludes application in the biological field above all, and involves incalculable risks in the preparation and use thereof.

The activation of hydroxy groups of the polysaccharides can also be achieved by conversion to carbonates, wherein either highly toxic phosgene or chlorocarbonates are employed as reagents (S. Barker, H. M. Disney, P. Somers: The reaction of dextran carbonate with amino acids and polypeptides, Carbohydrate Research 1972, 25, 237-241; M. S. Chaves, F. Arranz: Water-insoluble dextrans by grafting 2: Reaction of dextrans with normal-alkyl chloroformates, Chemical and enzymatic hydrolysis, Macromolecular Chemistry and Physics, 1985, 186, 17-29). However, the conversions mostly result in products with structural variability (for example, cyclic carbonate structures are formed in addition to monocarbonates), and insoluble products are formed because of cross-linking reactions. Nevertheless, cellulose carbonates were preferably reacted with amines having only one amino function, but also with diamines and oligoamines, to obtain either non-reactive products or, in the latter case, aminocelluloses of undefined structure, which are of interest in paper manufacturing, however (DE 38 36 599 A1). Derivatives of cellulose mainly served as starting materials. Cellulose itself could also be reacted according to the method described, but only up to a DS of 1.0-1.2 (a maximum DS of 3.0 can be reached). Also, nothing has been known to the art about the use thereof for the functionalization of surfaces.

The reaction of water-soluble polysaccharides, such as dextran, and water-soluble cellulose derivatives after activation with N,N'-carbonyldiimidazole and reaction with diamines yields cationic and water-soluble polyelectrolytes, which form polyplexes with DNA and can be employed for gene therapy (US 2011/0251265 A1). However, in this case too, a 20-fold to 30-fold excess of diamine must be employed to avoid cross-linking. Accordingly, major efforts are necessary for the purification of the products. According to the information provided in US 2011/0251265 A1, underivatized cellulose is explicitly not suitable for this procedure.

The direct modification of surfaces after activation with N,N'-carbonyldiimidazole and subsequent reaction with monoamines is also known, but does not involve a controlled reaction. Neither the structures nor the amount of groups can be selectively controlled. In particular, there are no free reactive primary amino groups (Sabrine Alila, Ana Maria Ferraria, Ana Maria Botelho do Rego, Sami Boufi: Controlled surface modification of cellulose fibers by amino derivatives using N,N-carbonyldiimidazole as activator, Carbohydrate Polymers 77, 2009, 553-562). Although this procedure is suitable for the in situ modification of fibers, it is not suitable for coating materials, because the reaction of the remaining hydroxy groups always leads to cross-linking and thus to the formation of insoluble products.

It is the object of the invention to perform surface functionalization with as low as possible a procedural effort and without the side effects described in the prior art, wherein the functionalized surface is to have a permanent chemical activity and a high degree of substitution (DS) of higher than 1.

Surprisingly, it has been found that dissolved oligo- or polysaccharide derivatives according to the following general formula I which contain at least one free functional group linked through a polar carbamate, linkage and a spacer (X), especially an amino group, and are contacted in such a solution with the surface to be treated cause a very advantageous surface functionalization with permanent chemical activity and a higher average degree of substitution (DS) as compared to the known prior art.

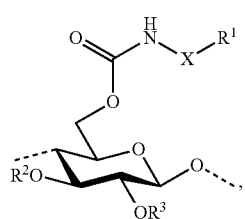
(I)

with $R^1$=NH$_2$, SH or OH;
$R^2$ or (independently) $R^3$=H or

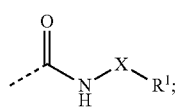

and

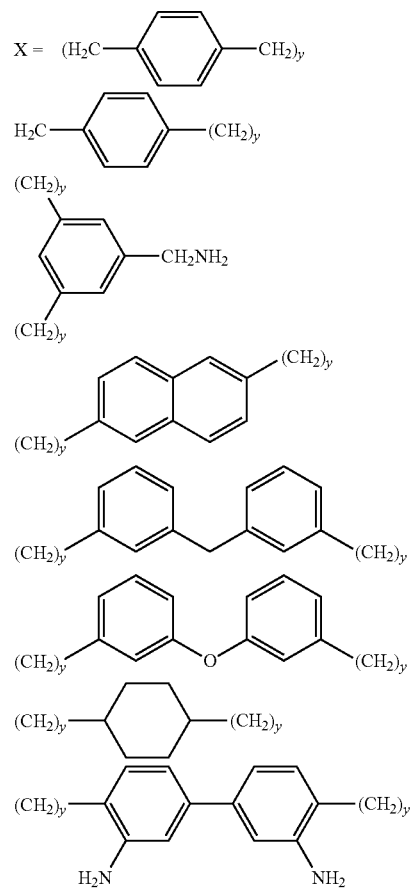

y = 0-10
X = (CH$_2$CH$_2$)$_y$ (CH$_2$CH$_2$NHCH$_2$CH$_2$)$_y$ (CH$_2$CH$_2$OCH$_2$CH$_2$)$_y$

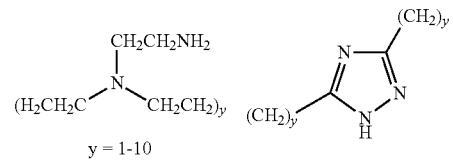

y = 1-10

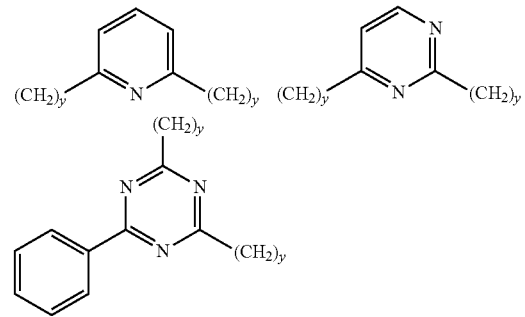

y = 0-10

In a preferred embodiment, the amino-substituted oligo- or polysaccharide is a homo- or heteroglycan, glucan, especially β-1-4-glucan, cellulose or chitin.

Advantageous compounds include an at least bifunctional amino-substituted oligo- or polysaccharide with a functional group of general formula II

—C(O)NH(X)NH$_2$,  (II)

wherein X represents any organic moiety, especially an aromatic, condensed aromatic, heterocyclic and/or heteroaromatic moiety, an alkyl and/or alkenyl moiety, which is also optionally substituted, or a moiety X as disclosed under (I).

The oligo- or polysaccharide may conveniently have a cellulose skeleton of general formula III

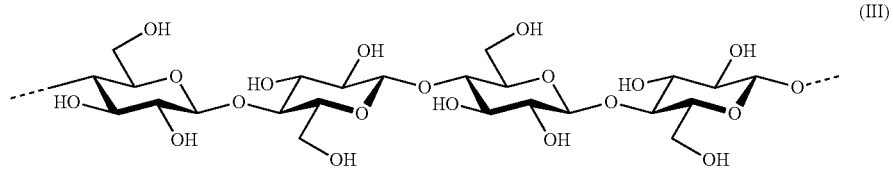
(III)

wherein the hydroxy groups of cellulose are at least in part substituted by OC(O)NH(X)NH$_2$, in which X represents any organic moiety, especially an aromatic, condensed aromatic, heterocyclic and/or heteroaromatic moiety, an alkyl and/or alkenyl moiety, which is optionally also substituted or includes a moiety X as disclosed under (I). The cellulose is advantageously employed with an average degree of polymerization (DP), based on its molecular mass, of from 30 to 1500, preferably within a range of from 50 to 300.

A hydroxy or thiol group may also be employed as said free functional group linked through a polar carbamate linkage and a spacer.

In terms of process technology, the surface functionalization can be effected in a per se known manner. A solution of the proposed oligo- or polysaccharide according to the general formula I is contacted with the surface to be functionalized, for which synthetic polymers and natural polymers, such as polysaccharides and proteins, glass, ceramic, silicon, metals, metal oxides including magnetic materials, are suitable, in particular. Such contact can be realized, for example, by dipping and subsequent washing with the solvent, or by spraying with different techniques. However, complicated methods, such as spin coating or dip coating, and other similarly known methods may also be applied.

The functionalization by the oligo- or polysaccharides according to the invention forms very thin strong layers containing reactive groups, especially amino groups, by adhesive self-assembly on the treated surface. "Strong layers" means that they cannot be removed in a subsequent treatment thereof, even if additional energy is input, for example, in an ultrasonic treatment. These surface layers produced by the invention cannot be removed even by the influence of solvents of a wide variety of electrolytic composition, and their strength and the chemical activity intended by such functionalization cannot be adversely affected.

Thus, the surface functionalization generates a material with new properties, which the starting materials do not have.

The hydrophobic-hydrophilic balance of the surface can be changed without particular effort. Thus, the effect of materials that are as such hydrophobic and may be porous, as employed in many filters of synthetic polymers, such as polyethylene, in water purification, can be significantly improved. The application of hydrophobic polymers in lateral or flow-through applications is also significantly improved. In addition, charges can be generated on the surface, and thus anion-exchanger properties can be produced. Also, proteins can be fixed thereby to the surface electrostatically and reversibly, which can be performed efficiently because of the high positive charge from the high average degree of substitution (DS). The high charge that can be achieved can be utilized for a selected orientation of proteins to be fixed.

The DS is defined as the quotient of the number of amines having at least two reactive amino functions introduced into the oligo- or polysaccharide by the aminolysis, divided by the number of original hydroxy groups of the oligo- or polysaccharide, multiplied by the number of original hydroxy groups per oligomer or polymer basic unit.

Said reactive groups, especially amino groups, form covalent bonds either directly, for example, with a wide variety of aldehydes, or indirectly after reaction with a dialdehyde or a dicarboxylic acid or its cyclic anhydride, whereby the molecule is firmly and irreversibly bound, as mentioned above. The detection and treatment reactions established in biochemistry, for example, with glutardialdehyde or succinic anhydride, can be simply performed as usual with the material composite layers formed according to the invention, and biomolecules, as well as antibodies, can be covalently fixed on the surface.

To obtain the oligo- or polysaccharides, the hydroxy groups are at least in part substituted by amino group. The oligo- or polysaccharide to be used according to the invention, which is constituted of basic units, is obtainable by derivatizing the hydroxy groups of an oligo- or polysaccharide into carbonate structures to obtain a derivatized oligo- or polysaccharide, followed by reaction of the derivatized oligo- or polysaccharide with an amine having at least two reactive amino functions with aminolysis to form the amino-substituted oligo- or polysaccharide having a DS of from 0.4 to 2.9, preferably from 0.8 to 2.0, more preferably from 1.0 to 1.5.

The synthesis of the oligo- or polysaccharide carbonates, preferably of the oligo- or polysaccharide phenylcarbonates, is effected in a homogeneous reaction of the oligo- or polysaccharide dissolved, for example, in N,N-dimethylacetamide/LiCl, with chloro- or fluorocarbonic acid esters. Soluble and structurally uniform products with DS values within a range of from 0.3 to 2.5 are available, which can be converted to the polysaccharide derivatives according to general formula I by aminolysis with the di- and oligoamines. The reaction with the amine does not require a molar excess, but the amine can be employed in equimolar amounts according to the desired average degree of substitution, wherein either the intrinsic selectivity of the di- or oligoamine, such as with aminobenzylamine, or a temporary protection of amino functions, for example, with the t-butyloxycarbonyl group (Boc group), can be utilized.

Thus, the benzylic amino group of aminobenzylamine is clearly more nucleophilic than the aromatic amino group, and therefore, reacts selectively with the carbonate groups. Cross-linking of the polymer chains through biscarbamate structures is prevented thereby even without a molar excess, and a polymer with a defined structure is obtained, since the aromatic amino group is always in a terminal position. Aliphatic diamines are protected on one side by means of a Boc group, and no molar excess of amine is required. In principle, the reaction can take place under very mild conditions (room temperature). Thus, no colored by-products are formed that could adversely affect biological or spectroscopic methods.

In contrast to deoxy amino structures, the carbamate linkage is planar because of the $sp^2$ carbon and has an optimum structure for interactions with surfaces. The carbamate structure is not reactive and cannot be protonated. Accordingly, the reactive primary amino function is present in the compounds according to the invention, so that an unambiguous reactivity and thus unambiguous structures result, which very advantageously yield unambiguous structure-property relationships in the applications.

In the following, the invention is further illustrated by means of Examples.

EXAMPLE 1

Synthesis of Cellulose Phenyl Carbonates:

Cellulose (Avicel, DP 220, 5 g, 30.8 mmol) was treated in 150 ml of dry DMAc with stirring at 120° C. for 2 hours; subsequently, 9 g of LiCl (212.3 mmol) was added at 90° C. The suspension was stirred until a clear solution is obtained (5-24 hours). The cellulose solution was cooled down to 0° C. in a 250 ml double wall reactor, and equivalent amounts of pyridine and carbonic acid phenyl ester chloride were added under an $N_2$ atmosphere. After a reaction time of 4 hours at 0° C., the mixture was precipitated in 1.5 liters of ice-water, the precipitate was filtered off and washed twice with 1 liter of water and twice with 1 liter of ethanol. The product was dried under vacuum at 40° C. and subsequently reprecipitated from 120 ml of acetone.

| AGU/carbonic acid phenyl ester chloride molar ratio | No. | DS | Yield (%) |
|---|---|---|---|
| 1.0:1.0 | 1 | 0.84 | 92 |
| 1.0:1.5 | 2 | 1.17 | 94 |
| 1.0:3.0 | 3 | 1.49 | 99 |
| 1.0:5.0 | 4 | 1.75 | 98 |
| 1.0:10.0 | 5 | 1.98 | 94 |

Spectroscopic Data from Sample 1:

FT-IR (KBr): 3460 cm$^{-1}$ ν (OH), 3070 cm$^{-1}$ ν ($CH_{arom}$), 2900 cm$^{-1}$ ν (CH), 1766 cm$^{-1}$ ν (C=O), 1254 cm$^{-1}$ ν (C—O—C)

$^1$H NMR (250 MHz, DMSO-$d_6$): δ [ppm]=7.38-7.25 ($H_{arom}$), 5.60-3.16 (H-1-H-6 and OH)

$^{13}$C NMR (250 MHz, DMSO-$d_6$): δ [ppm]=153.4 (C=O), 151.2 ($C_{ipso}$), 130.0 (C—$H_m$), 126.6 (C—$H_p$), 121.8 (C—$H_o$), 102.7 (C-1), 79.1, 74.3, 73.0, 72.3 (C-4, C-5, C-3, C-2), 67.7 (C-6$_s$), 60.8 (C-6).

EXAMPLE 2

Aminolysis of Cellulose Phenyl Carbonates:

a) With N-Tert-Butoxycarbonyldiamine:

Cellulose phenyl carbonate (2 g) in 15 ml of DMF was mixed with a solution of the corresponding amine (see below) in 15 ml of DMF with vigorous stirring, and the reaction mixture was stirred at 60° C. for 24 hours. Subsequently, the product was precipitated in 400 ml of water, filtered off, washed twice with water, twice with sodium hydrogencarbonate solution, and then again twice with water. After drying under vacuum at 40° C., a white powder was obtained.

b) With p-Aminobenzylamine:

Cellulose phenyl carbonate (1 g) in 8 ml of DMF was mixed with a solution of p-aminobenzylamine (2-3 equivalents per carbonate group) in 8 ml of DMF with vigorous stirring, and the reaction mixture was stirred at 60° C. for 24 hours. Subsequently, the product was precipitated in 150 ml of 2-propanol, filtered off, and washed four times with 2-propanol. After drying under vacuum at 40° C., a white powder was obtained.

| $DS_{carbonate}$ | Amine | No. | DS | DS yield (%) |
|---|---|---|---|---|
| 1.49 | N-Boc-EDA | 6 | 1.35 | 91 |
| 1.75 | N-Boc-EDA | 7 | 1.75 | 100 |
| 1.75 | N-Boc-BDA | 8 | 1.71 | 98 |
| 1.75 | N-Boc-DA-10 | 9 | 1.69 | 97 |
| 1.98 | N-Boc-EDA | 10 | 1.77 | 89 |
| 1.75 | p-APA | 11 | 1.64 | 94 |

N-Boc-EDA: N-tert-butoxycarbonyl-1,2-ethanediamine,
N-Boc-BDA: N-tert-butoxycarbonyl-1,4-butanediamine,
N-Boc-DA-10: N-tert-butoxycarbonyl-2,2'-(ethylenedioxy) diethylamine, p-ABA: p-aminobenzylamine Spectroscopic Data from Sample 7:

FTIR (KBr): 1701 cm$^{-1}$ ($ν_{C=O}$), $^{13}$C NMR (100 MHz, DMSO-$d_6$): δ [ppm]=156 (C=O), 102.9 (C-1), 101.1 (C-1'), 78.3 ($CMe_3$), 82-72 (C-2, C-3, C-4, C-5), 63.4 (C-6), $CH_2$ hidden by the solvent signal, 28.7 ($CH_3$).

EXAMPLE 3

Deprotection of the Boc Protecting Group:

Cellulose carbamate (2 g) was dissolved in 40 ml of TFA and subsequently stirred at room temperature for 15 min. The product was isolated by precipitation in 400 ml of 2-propanol, and then washed four times with 100 ml each of the precipitant. After drying under vacuum at 40° C., the product was dissolved in 50 ml of water and treated over night with the ion-exchanger Amberlite IRA-410 (chloride form). Subsequently, the solution obtained was freeze-dried.

Spectroscopic Data for Aminoethyl Cellulose Carbamates:

FTIR (KBr): 1710 cm$^{-1}$ ($ν_{C=O}$), $^{13}$C NMR (100 MHz, $D_2O$): δ [ppm]=158 (C=O), 102.9 (C-1), 101.8 (C-1'), 81-71 (C-2, C-3, C-4, C-5), 63.0 (C-6), 39.6 ($CH_2$), 38.1 ($CH_2$).

EXAMPLE 4

Coating of Gold Surfaces:

Gold-coated silicon wafers were placed into piranha solution (sulfuric acid/hydrogen peroxide, 2:1) for 3 hours before the coating in order to clean the surface. Subsequently, the supports were thoroughly rinsed with distilled water. The wafers were coated by means of a spin coater (MicroTec Delta 10TT, Süss) at 200 rotations per minute with a 1% aqueous solution of aminocellulose ethyl carbamate, DS 1.43, and subsequently rinsed with distilled water. The contact angle (water) of the coated surface is 61°.

EXAMPLE 5

Coating of a Gold Single Crystal:

An Au(111) substrate was treated with concentrated sulfuric acid for 48 hours, washed with distilled water and absolute ethanol, dried in a nitrogen flow, and subsequently heated with a butane gas burner for 5-10 min until it glowed. Then, the surface was measured with an atomic force microscope (Dualscope C-21, DME), and subsequently treated with a 0.1% solution of aminocellulose ethyl carbamate, DS 1.43. Subsequently, it was intensively washed with water. The roughness (RMS, root mean square) of the surface increased from 80 pm (Au(111) substrate) to 260 pm by the functionalization, which demonstrates the coating.

EXAMPLE 6

Quantification of the Coating of Gold by Means of QCM:

The adsorption of aminoethylcellulose carbamate on gold surfaces was demonstrated with a quartz crystal microbalance (Q-Sence). The QCM substrates were cleaned with piranha solution before the coating, rinsed with distilled water, and subsequently dried in a nitrogen flow. The crystals were flooded by a solution of the aminoethylcellulose carbamate (concentrations of 0.001-1%) and subsequently washed with water until the equilibrium frequency was reached. For concentrations of 0.1%, an adsorbed mass of 200 ng per $cm^2$ was detected.

EXAMPLE 7

Coating of Glass:

Glass supports (beads Ø 1.5 mm, KGM Fulda) were cleaned with piranha solution before the coating and subsequently rinsed with distilled water. The glasses were immersed in an aqueous solution of 0.1% aminocellulose ethyl carbamate, DS 1.43, for 15 min, and subsequently washed with distilled water.

To determine the surface density of amino groups, they were derivatized with 4,4'-dimethoxytrityl chloride, treated with methanolic perchloric acid, and the concentration of dimethoxytrityl cations was measured by UV/Vis spectroscopy (498 nm). For aminoethylcellulose carbamate layers on glass, a density of amino groups of 0.6-0.8 nmol per $cm^2$ was found.

EXAMPLE 8

Coating of Polyethylene:

Polyethylene supports were treated in an oxygen plasma and thereafter placed in an aqueous solution of 0.1% aminocellulose ethyl carbamate, DS 1.43, for 15 min. Subsequently, the supports were washed with distilled water. The concentration of amino groups was 0.30 nmol per $cm^2$.

EXAMPLE 9

Immobilization of Anti-h CRP Antibodies (Clone 6404, Medix) on $NH_2$-Functionalized Supports with the Homobifunctional Reagent Glutardialdehyde:

1. Activation of the $NH_2$-Functionalized Surfaces by Glutardialdehyde:

Ten $NH_2$-functionalized PE microfilters (h=2.5 mm, Ø=5 mm, type 180, Porex) were stirred with 2 ml of a 5% aqueous glutardialdehyde solution at room temperature for 15 minutes. After four washes with 3 ml each of water, the microfilters were available for immobilization.

2. Immobilization of Anti-h CRP Antibodies (Clone 6404, Medix) on the Glutaraldehyde-Activated Surfaces:

To the PE microfilters treated as described under 1., 75 µg of anti-h CRP antibodies (clone 6404, Medix) in 2 ml of bicarbonate buffer (0.1 M, pH 9.5) was added, and stirred at room temperature for four hours. To block the remaining activated surface, 5 µl of ethanolamine was added to the immobilization solution after the immobilization, and stirring was continued for another two hours. After four washes with 3 ml each of water and subsequent drying in an air flow, CRP-affine surfaces were obtained. 6.0 µg per microfilter was successfully immobilized, wherein 30% of the immobilized antibodies were active.

EXAMPLE 10

Immobilization of Anti-h CRP Antibodies (Clone 6404, Medix) on COOH-Functionalized Supports by Means of EDC/s-NHS Chemistry:

1. Refunctionalization of the $NH_2$-Functionalized Surfaces and Subsequent Activation of the COOH-Functionalized Surfaces:

Ten $NH_2$-functionalized PE microfilters were stirred in 2 ml of a solution of succinic anhydride (c=40 mg/ml) and 5 µl of pyridine in N,N-dimethylformamide at room temperature for 16 hours. Carboxy groups were introduced on the PE microfilters by the reaction of the succinic anhydride with the amino groups of the surface. After repeated washes of the surfaces with 3 ml each of water, the carboxy groups could be activated by 1-ethyl-3-(3-dimethylamino-propyl) carbodiimide (EDC) and sulfo-N-hydroxysuccinimide (s-NHS). Thus, the microfilters were stirred in 2 ml of a 2-(N-morpholino)ethanesulfonic acid buffered solution (0.1 M, pH 5.5) with EDC (2 mM) and s-NHS (5 mM), and stirred for 30 minutes.

2. Immobilization of Anti-h CRP Antibodies (Clone 6404, Medix) on the Activated COOH Surfaces:

The immobilization of anti-h CRP antibodies (clone 6404, Medix) was effected after washing with water the microfilters treated as described under 1, followed by the addition of 75 µg of anti-h CRP antibodies (clone 6404, Medix) in 2 ml of phosphate buffers (0.1 M, pH 7.4) and stirring at room temperature for two hours. The remaining activated carboxy groups were blocked by adding 5 µl of ethanolamine to the immobilization solution and stirring for another 60 minutes. After four washes with 3 ml each of water and subsequent drying in an air flow, CRP-affine surfaces were obtained. 7.0 µg per microfilter was successfully immobilized, wherein 30% of the immobilized antibodies were active.

EXAMPLE 11

Immobilization of Anti-h CRP Antibodies (Clone 6404, Medix) on $NH_2$-Functionalized Supports with the Reagent Ascorbic Acid:

1. Activation of the $NH_2$-Functionalized Surfaces by Ascorbic Acid:

Ten $NH_2$-functionalized PE microfilters (h=2.5 mm, Ø=5 mm, type 180, Porex) were stirred with 2 ml of a saturated solution of ascorbic acid in N,N-dimethylformamide at room temperature for 15 minutes. After four washes with 3 ml each of water, the microfilters were available for immobilization.

2. Immobilization of Anti-h CRP Antibodies (Clone 6404, Medix) on the Ascorbic Acid-Activated Surfaces:

To the PE microfilters treated as described under 1., 75 µg of anti-h CRP antibodies (clone 6404, Medix) in 2 ml of bicarbonate buffer (0.1 M, pH 9.5) was added, and stirred at room temperature for 16 hours. To block the remaining activated surface, 5 µl of ethanolamine was added to the immobilization solution after the immobilization, and stirring was continued for another two hours. After four washes with 3 ml each of water and subsequent drying in an air flow, CRP-affine surfaces were obtained. 5.2 µg per microfilter was successfully immobilized, wherein 35% of the immobilized antibodies were active.

EXAMPLE 12

Immobilization of Anti-h CRP Antibodies (Clone 6404, Medix) on $NH_2$-Functionalized Supports with the Reagent Benzoquinone:

1. Activation of the $NH_2$-Functionalized Surfaces by Benzoquinone:

Ten $NH_2$-functionalized PE microfilters (h=2.5 mm, Ø=5 mm, type 180, Porex) were stirred with 2 ml of a saturated solution of benzoquinone in N,N-dimethylformamide at room temperature for 15 minutes. After four washes with 3 ml each of DMF and then twice with water, the microfilters were available for immobilization.

2. Immobilization of Anti-h CRP Antibodies (Clone 6404, Medix) on the Benzoquinone-Activated Surfaces:

To the PE microfilters treated as described under 1., 75 µg of anti-h CRP antibodies (clone 6404, Medix) in 2 ml of bicarbonate buffer (0.1 M, pH 9.5) was added, and stirred at room temperature for 16 hours. To block the remaining activated surface, 5 µl of ethanolamine was added to the immobilization solution after the immobilization, and stirring was continued for another two hours. After four washes with 3 ml each of water and subsequent drying in an air flow, CRP-affine surfaces were obtained. 6.0 µg per microfilter was successfully immobilized, wherein 36% of the immobilized antibodies were active.

EXAMPLE 13

Immobilization of anti-h CRP antibodies (clone 6404, Medix) on $NH_2$-functionalized supports with the reagent 4,4'-dihydroxybiphenyl diglycidyl ether:

1. Activation of the $NH_2$-functionalized surfaces by 4,4'-dihydroxybiphenyl diglycidyl ether:

Ten $NH_2$-functionalized PE microfilters (h=2.5 mm, Ø=5 mm, type 180, Porex) were stirred with 2 ml of a 5% aqueous solution of 4,4'-dihydroxybiphenyl diglycidyl ether at room temperature for 15 minutes. After four washes with 3 ml each of water, the microfilters were available for immobilization.

2. Immobilization of anti-h CRP antibodies (clone 6404, Medix) on the 4,4'-dihydroxybiphenyl diglycidyl ether activated surfaces:

To the PE microfilters treated as described under 1., 75 µg of anti-h CRP antibodies (clone 6404, Medix) in 2 ml of bicarbonate buffer (0.1 M, pH 9.5) was added, and stirred at room temperature for 16 hours. To block the remaining activated surface, 5 µl of ethanolamine was added to the immobilization solution after the immobilization, and stirring was continued for another two hours. After four washes with 3 ml each of water and subsequent drying in an air flow, CRP-affine surfaces were obtained. 5.5 µg per microfilter was successfully immobilized, wherein 35% of the immobilized antibodies were active.

EXAMPLE 14

Immobilization of Anti-h CRP Antibodies (Clone 6404, Medix) on COOH-Functionalized Supports by Adhesive Interactions:

1. Refunctionalization of the $NH_2$-Functionalized Surfaces for Introducing Carboxy Groups on the Surface:

Ten $NH_2$-functionalized PE microfilters were stirred in 2 ml of a solution of succinic anhydride (c=40 mg/ml) and 5 µl of pyridine in N,N-dimethylformamide at room temperature for 16 hours. Carboxy groups were introduced on the PE microfilters by the reaction of the succinic anhydride with the amino groups of the surface.

2. Immobilization of Anti-h CRP Antibodies (Clone 6404, Medix) on the COOH-Functionalized Surfaces:

The immobilization of anti-h CRP antibodies (clone 6404, Medix) was effected after washing with water the microfilters treated as described under 1, followed by the addition of 75 µg of anti-h CRP antibodies (clone 6404, Medix) in 2 ml of a 2-(N-morpholino)ethanesulfonic acid buffered solution (0.1 M, pH 7.4) and stirring at room temperature for two hours. The remaining activated carboxy groups were blocked by adding 10 µl of a 10% aqueous bovine serum albumin (BSA) solution to the immobilization solution and stirring for another 60 minutes. After four washes with 3 ml each of water and subsequent drying in an air flow, CRP-affine surfaces were obtained. 5.9 µg per microfilter was successfully immobilized, wherein 15% of the immobilized antibodies were active.

EXAMPLE 15

Immobilization of Anti-h CRP Antibodies (Clone 6404, Medix) on $SO_3H$-Functionalized Supports by Adhesive Interactions:

1. Refunctionalization of the $NH_2$-Functionalized Surfaces for Introducing Sulfonic Acid Groups on the Surface:

Ten $NH_2$-functionalized PE microfilters were stirred in 2 ml of a saturated solution of 4,4'-biphenyldisulfonic acid dichloride in dry diethyl ether at room temperature for 15 minutes. Sulfonic acid chloride groups were introduced on the PE microfilters by the reaction of the 4,4'-biphenyldisulfonic acid dichloride with the amino groups of the surface. These amino groups were hydrolyzed by treatment with 2 ml of a 0.1 M hydrochloric acid over night to obtain sulfonic acid groups on the surface.

2. Immobilization of Anti-h CRP Antibodies (Clone 6404, Medix) on the $SO_3H$-Functionalized Surfaces:

The immobilization of anti-h CRP antibodies (clone 6404, Medix) was effected after washing with water the microfilters treated as described under 1, followed by the addition of 75 µg of anti-h CRP antibodies (clone 6404, Medix) in 2 ml of a 2-(N-morpholino)ethanesulfonic acid buffered solution (0.1 M, pH 7.4) and stirring at room temperature for two hours. The remaining activated carboxy groups were blocked by adding 10 µl of a 10% aqueous bovine serum albumin (BSA) solution to the immobilization solution and stirring for another 60 minutes. After four washes with 3 ml each of water and subsequent drying in an air flow, CRP-affine surfaces were obtained. 5.8 µg per microfilter was successfully immobilized, wherein 15% of the immobilized antibodies were active.

The invention claimed is:
1. A process for the functionalization of a surface, which comprises at least one of synthetic polymers, natural polymers, paper, glass, ceramic, silicon, metals, or metal oxides, and is contacted, for surface functionalization, with a solution containing at least one compound for forming a material composite with the surface material, wherein as said at least one compound for forming the material composite, a dissolved oligo- or polysaccharide derivative is employed which has at least one free functional group $R^1$ linked through a polar carbamate linkage and a spacer (X), according to the general formula I:

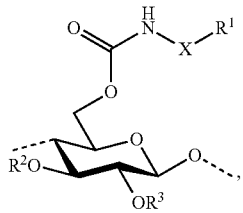

(I)

with $R^1$=$NH_2$, SH or OH;
and
$R^2$ and (independently) $R^3$=H or

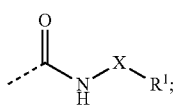

and

X = 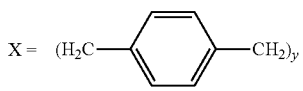

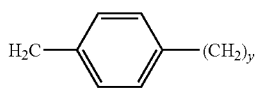

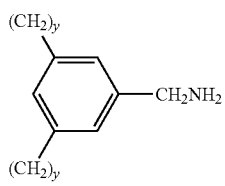

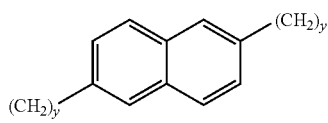

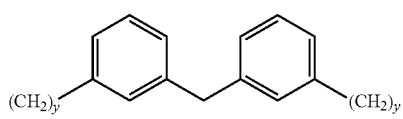

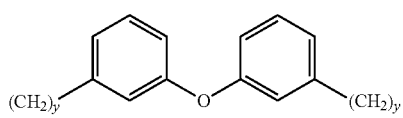

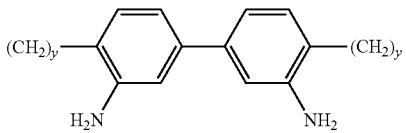

y = 0-10

X = $(CH_2CH_2)_y$, $(CH_2CH_2NHCH_2CH_2)_y$, $(CH_2CH_2OCH_2CH_2)_y$

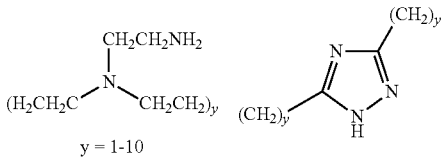

y = 1-10

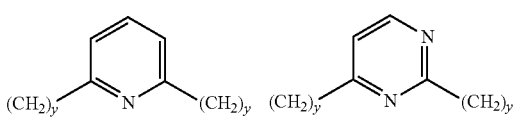

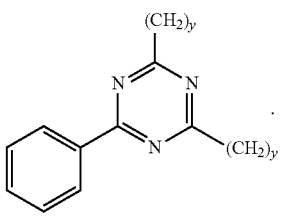

y = 0-10

2. The process according to claim 1, wherein a hydroxy group is provided as at least one functional group $R^1$.

3. The process according to claim 1, wherein a thiol group is provided as at least one functional group $R^1$.

4. The process according to claim 1, wherein an amino group is provided as at least one functional group $R^1$.

5. The process according to claim 1, wherein a homo- or heteroglycan is used as said oligo- or polysaccharide.

6. The process according to claim 1, wherein glucan, cellulose or chitin, is used as said oligo- or polysaccharide.

7. The process according to claim 1, wherein an at least bifunctional amino-substituted oligo- or polysaccharide with a functional group of general formula II is provided:

—C(O)NH(X)NH$_2$, (II)

wherein X represents any organic moiety which is optionally substituted, or a moiety X as disclosed under (I).

8. The process according to claim 1, wherein the oligo- or polysaccharide has a cellulose skeleton of general formula III

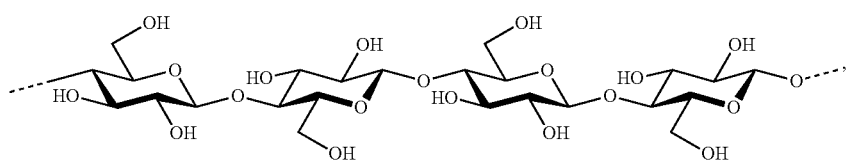

(III)

wherein the hydroxy groups of cellulose are at least in part substituted by OC(O)NH(X)NH$_2$, in which X represents any organic moiety an alkyl and/or alkenyl moiety, which is optionally substituted or includes a moiety X as disclosed under (1).

9. The process according to claim 6, wherein a cellulose with an average degree of polymerization (DP), based on its molecular mass, of from 30 to 1500 is employed as said oligo- or polysaccharide.

10. The process according to claim 1, wherein the natural polymers are selected from the group consisting of polysaccharides and proteins.

11. The process according to claim 6, wherein the glucan is β-1-4-glucan.

12. The process according to claim 7, wherein the organic moiety is selected from the group consisting of an aromatic moiety, a condensed aromatic moiety, a heterocyclic moiety, a heteroaromatic moiety, an alkyl moiety, and an alkenyl moiety.

13. The process according to claim 8, wherein the organic moiety is selected from the group consisting of an aromatic moiety, a condensed aromatic moiety, a heterocyclic moiety, a heteroaromatic moiety, an alkyl moiety, and an alkenyl moiety.

14. The process according to claim 9, wherein the average degree of polymerization is within a range of from 50 to 300.

* * * * *